United States Patent
Endo et al.

(10) Patent No.: US 9,480,456 B2
(45) Date of Patent: Nov. 1, 2016

(54) IMAGE PROCESSING APPARATUS THAT SIMULTANEOUSLY DISPLAYS TWO REGIONS OF INTEREST ON A BODY MARK, PROCESSING METHOD THEREOF AND STORAGE MEDIUM

(75) Inventors: Takaaki Endo, Urayasu (JP); Kiyohide Satoh, Kawasaki (JP); Ryo Ishikawa, Kawasaki (JP); Hiroyuki Yamamoto, Chigasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 502 days.

(21) Appl. No.: 13/437,663

(22) Filed: Apr. 2, 2012

(65) Prior Publication Data

US 2012/0262460 A1 Oct. 18, 2012

(30) Foreign Application Priority Data

Apr. 13, 2011 (JP) ................................ 2011-089538

(51) Int. Cl.
| | | |
|---|---|---|
| *G06T 11/20* | (2006.01) | |
| *A61B 8/08* | (2006.01) | |
| *A61B 5/055* | (2006.01) | |
| *A61B 5/00* | (2006.01) | |
| *A61B 8/00* | (2006.01) | |

(52) U.S. Cl.
CPC ............. *A61B 8/0825* (2013.01); *A61B 5/055* (2013.01); *A61B 5/4312* (2013.01); *A61B 8/4263* (2013.01); *A61B 8/5261* (2013.01)

(58) Field of Classification Search
None
See application file for complete search history.

(56) References Cited

U.S. PATENT DOCUMENTS

| | | | |
|---|---|---|---|
| 6,226,418 B1 * | 5/2001 | Miller et al. .................. | 382/294 |
| 7,386,089 B2 | 6/2008 | Endo et al. ....................... | 378/5 |
| 7,738,683 B2 * | 6/2010 | Cahill et al. .................. | 382/128 |
| 8,105,240 B2 | 1/2012 | Kamiyama et al. .......... | 600/463 |
| 2006/0174065 A1 * | 8/2006 | Kuzara ..................... | A61B 8/00 711/123 |
| 2006/0251301 A1 | 11/2006 | McNamara, Jr. et al. .... | 382/128 |
| 2007/0010743 A1 * | 1/2007 | Arai ........................ | A61B 8/13 600/443 |

(Continued)

FOREIGN PATENT DOCUMENTS

| | | |
|---|---|---|
| JP | 2007-236823 | 9/2007 |
| JP | 2008-086742 | 4/2008 |

(Continued)

OTHER PUBLICATIONS

Behrenbruch et al "Prone-Supine Breast MRI Registration for Surgical Visualisation", Proc. Medical Image Understanding & Analysis, pp. 109-112, 2001.*

(Continued)

*Primary Examiner* — Ryan R Yang
*Assistant Examiner* — Patrick F Valdez
(74) *Attorney, Agent, or Firm* — Fitzpatrick, Cella, Harper & Scinto

(57) ABSTRACT

An image processing apparatus displays the position of a region of interest in a target object with a first shape on a body mark that represents the target object. Here, the image processing apparatus includes an image acquisition unit configured to acquire an image of a target object with a second shape that is different from the first shape, a converter configured to convert the position of the region of interest in the target object with the second shape into a corresponding position in the target object with the first shape, and a composition unit configured to display the converted position of the region of interest on the body mark.

9 Claims, 13 Drawing Sheets

(56) References Cited

U.S. PATENT DOCUMENTS

| | | | |
|---|---|---|---|
| 2007/0239006 A1* | 10/2007 | Kamiyama et al. | 600/437 |
| 2009/0076385 A1* | 3/2009 | Jackson et al. | 600/437 |
| 2009/0264758 A1* | 10/2009 | Fujita et al. | 600/443 |
| 2009/0285460 A1 | 11/2009 | Ishikawa et al. | 382/128 |
| 2010/0074488 A1 | 3/2010 | Ishikawa et al. | 382/128 |
| 2010/0222680 A1* | 9/2010 | Hamada | 600/443 |
| 2011/0125020 A1* | 5/2011 | Kondou | A61B 5/06 600/443 |
| 2011/0208052 A1* | 8/2011 | Entrekin | A61B 8/0825 600/437 |
| 2011/0262015 A1 | 10/2011 | Ishikawa et al. | 382/128 |

FOREIGN PATENT DOCUMENTS

| | | |
|---|---|---|
| JP | 2008-515519 | 5/2008 |
| JP | 2008-518684 | 6/2008 |
| JP | 2008-279272 | 11/2008 |
| JP | 2009-268735 | 11/2009 |
| JP | 2010-162058 | 7/2010 |
| JP | 2010158386 A * | 7/2010 |
| JP | 2010-172499 | 8/2010 |
| WO | WO 2008/035445 A | 3/2008 |
| WO | WO 2011007312 A1 * | 1/2011 |

OTHER PUBLICATIONS

Kaus et al "Deformable Image Registration for Radiation Therapy Planning: Algorithms and Applications", Biomechanical Systems Technology, Chapter 1, pp. 1-28, vol. 1: Computation Methods, ISBN: 978-981-270-981-3, Dec. 2003.*

T. Carter et al., "MR Navigated Breast Surgery: Method and Initial Clinical Experience", *MICCAI* 2008, Part II, LNCS 5242, pp. 356-363 (2008).

* cited by examiner

F I G. 10
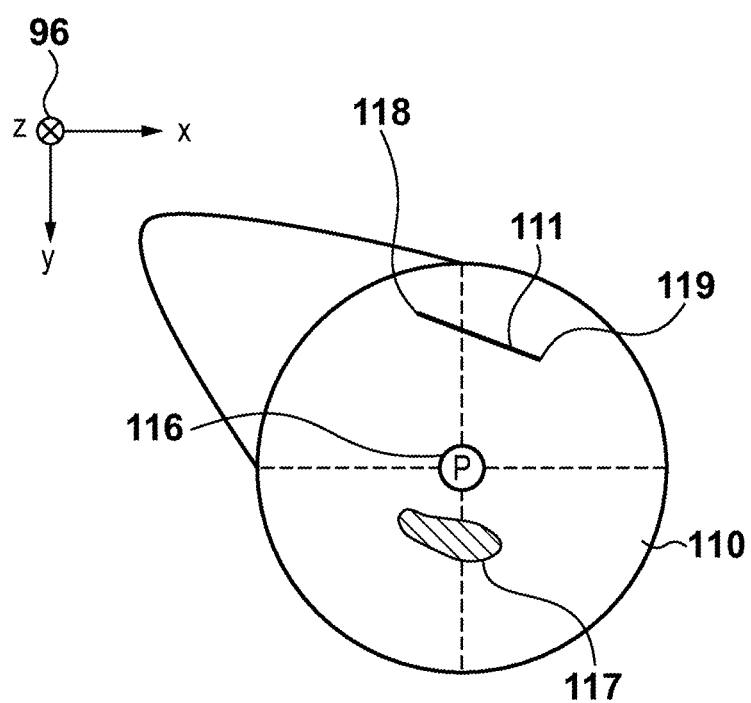

FIG. 13
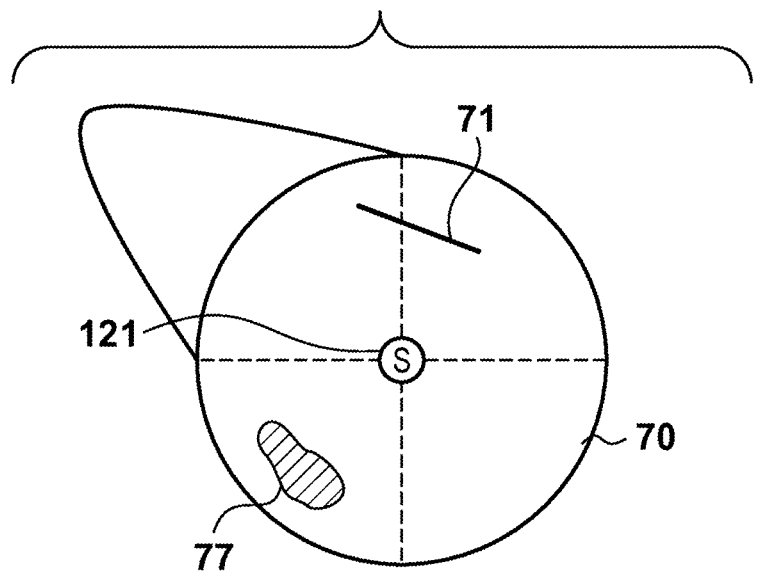
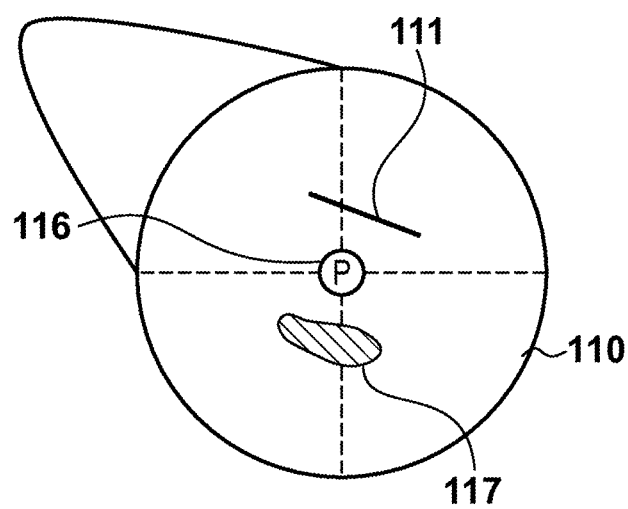

FIG. 14
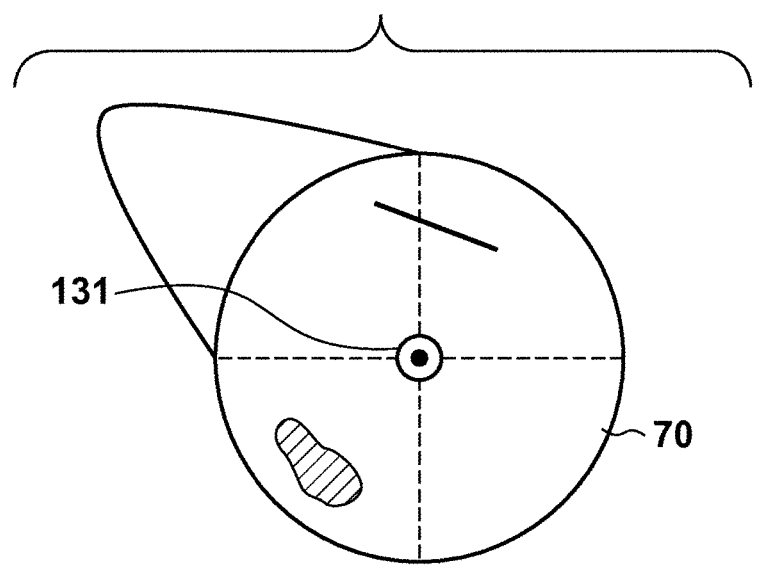
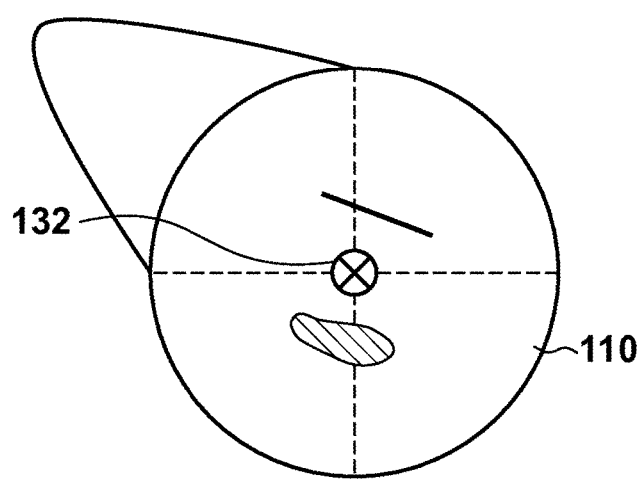

IMAGE PROCESSING APPARATUS THAT SIMULTANEOUSLY DISPLAYS TWO REGIONS OF INTEREST ON A BODY MARK, PROCESSING METHOD THEREOF AND STORAGE MEDIUM

BACKGROUND OF THE INVENTION

1. Field of the Invention

The present invention relates to an image processing apparatus, and a processing method and a non-transitory computer-readable storage medium for the same.

2. Description of the Related Art

There is a conventional technique whereby information about a lesion within a medical image, or probe position information is displayed on a body mark that represents the approximate shape of a target object in order to help manipulate the probe during an ultrasound examination or to produce a medical document such as an electronic chart or an image diagnostic report.

For example, Japanese Patent Laid-Open No. 2008-086742 (hereinafter referred to as Literature 1) discloses a technique for finding a conversion rule that performs coordinate conversion from a position on a patient's breast during an ultrasound examination to a standard body mark that represents a breast, and displaying the position of an ultrasonic probe on the body mark (after normalizing it to a body mark coordinate system). Also, Japanese Patent Laid-Open No. 2008-279272 (hereinafter referred to as Literature 2) discloses a technique for producing a 3D body mark by the volume rendering of a target object imaged by MRI apparatus or X-ray CT apparatus, and superposing a display of a graph representing the position of the probe and the position of a lesion on the 3D body mark. With this technique, probe manipulation can be facilitated when a physician is looking for a lesion during ultrasound examination.

In the area of breast oncology, image diagnosis is sometimes performed by a procedure in which the condition of a lesion is imaged and observed using an ultrasound apparatus after identifying the position of the lesion within an image of a breast captured with an MRI apparatus.

In a typical imaging protocol in a breast oncology department, imaging with an MRI apparatus is usually performed in a prone position (face down), and imaging with an ultrasound apparatus in a supine position (face up). In such situations, the physician first identifies the position of the lesion from an MRI image taken in a prone position. Then, deformation of the breast (physical deformation) attributable to different imaging sites is taken into account, and the position of the lesion in the supine position is estimated from the identified position of the lesion. An image is then taken of this estimated position with an ultrasound apparatus.

However, in some cases there is an extremely large amount of breast deformation (physical deformation) attributable to different imaging sites, and the position of the lesion in a supine position estimated by the physician may be very different from the actual position.

Such situations can be dealt with, for example, by using the method of "T. Carter, C. Tanner, N. B. Newman, D. Barratt and D. Hawkes, MR Navigated Breast Surgery Method and Initial Clinical Experience" (MICCAI 2008, Part II, LNCS 5242, pp. 356-363, 2008) (hereinafter referred to as Literature 3), subjecting an MRI image taken in a prone position to physical conversion, and virtually producing an MRI image taken in a supine position. With this method is used, the position of a lesion on the supine position MRI image produced virtually can be calculated on the basis of physical conversion information from prone position to supine position. Also, the position of the lesion on this image can be found directly by the physician by reading the virtual supine position MRI image.

If the precision is high in this physical conversion, then when the lesion is imaged from a subject in a supine position, the actual lesion will be close to the lesion shown in the virtual supine position MRI image, so imaging should be performed in this region.

Using this physical conversion technique and the method disclosed in the above-mentioned Literature 2 as a basis, a supine position 3D body mark can be produced by performing physical conversion of an image of a target object captured in a prone position into an image of a target object captured in a supine position. Furthermore, probe manipulation can be facilitated when a physician is searching for a lesion during an ultrasound examination by superposing a display of a graph representing the position of the lesion over this 3D body mark.

With the prior art discussed in Literature 1, information about the lesion indicated by the prone position MRI image could not be displayed on the body mark. Even if a conversion rule could be found that would do coordinate conversion of the position of a lesion on a body mark on the basis of the external shape of a breast obtained from an MRI image, the displayed position of the lesion will deviate from the actual position. The reason this deviation occurs is that the difference in the physical distortion state of the breast during imaging between ultrasound and MRI is not taken into account. Accordingly, probe manipulation cannot be properly facilitated.

Also, even if a supine position 3D body mark is produced on the basis of the methods in the above-mentioned Literature 3 and 2, the shape of the body mark will not be simplified or normalized, so making a contrast to a standard position expression A region, B region, etc.) is not intuitive. Accordingly, this is not suited to use in a medical document such as an electronic chart or an image diagnostic report.

SUMMARY OF THE INVENTION

The present invention provides a technique with which regions of interest in a target object that have been imaged in different shapes can be combined and displayed on a body mark on which a target object is displayed.

According to a first aspect of the present invention there is provided an image processing apparatus that displays the position of a region of interest in a target object with a first shape on a body mark that represents the target object, comprising: an image acquisition unit configured to acquire an image of the target object with a second shape that is different from the first shape; a converter configured to convert the position of the region of interest in the target object with the second shape into a corresponding position in the target object with the first shape; and a composition unit configured to display the converted position of the region of interest on the body mark.

According to a second aspect of the present invention there is provided a processing method for an image processing apparatus that displays the position of a region of interest in a target object with a first shape on a body mark that represents the target object, the method comprising: acquiring an image of the target object with a second shape that is different from the first shape; converting the position of the region of interest in the target object with the second shape into a corresponding position in the target object with the first shape; and displaying the converted position of the region of interest on the body mark.

Further features of the present invention will be apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 10 is a diagram of an example of a body mark used for a prone position;

FIG. 13 is a diagram of an example of a body mark according to Embodiment 3; and FIG. 14 is a diagram of a modification example of a body mark according to Embodiment 3.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

In the embodiments that follow, the description will be of a case in which a human breast serves as the target object, and the region of interest is a three-dimensional region that represents the spread of lesion in this breast (hereinafter referred to as a lesion region).

Embodiment 1

Figure 1:
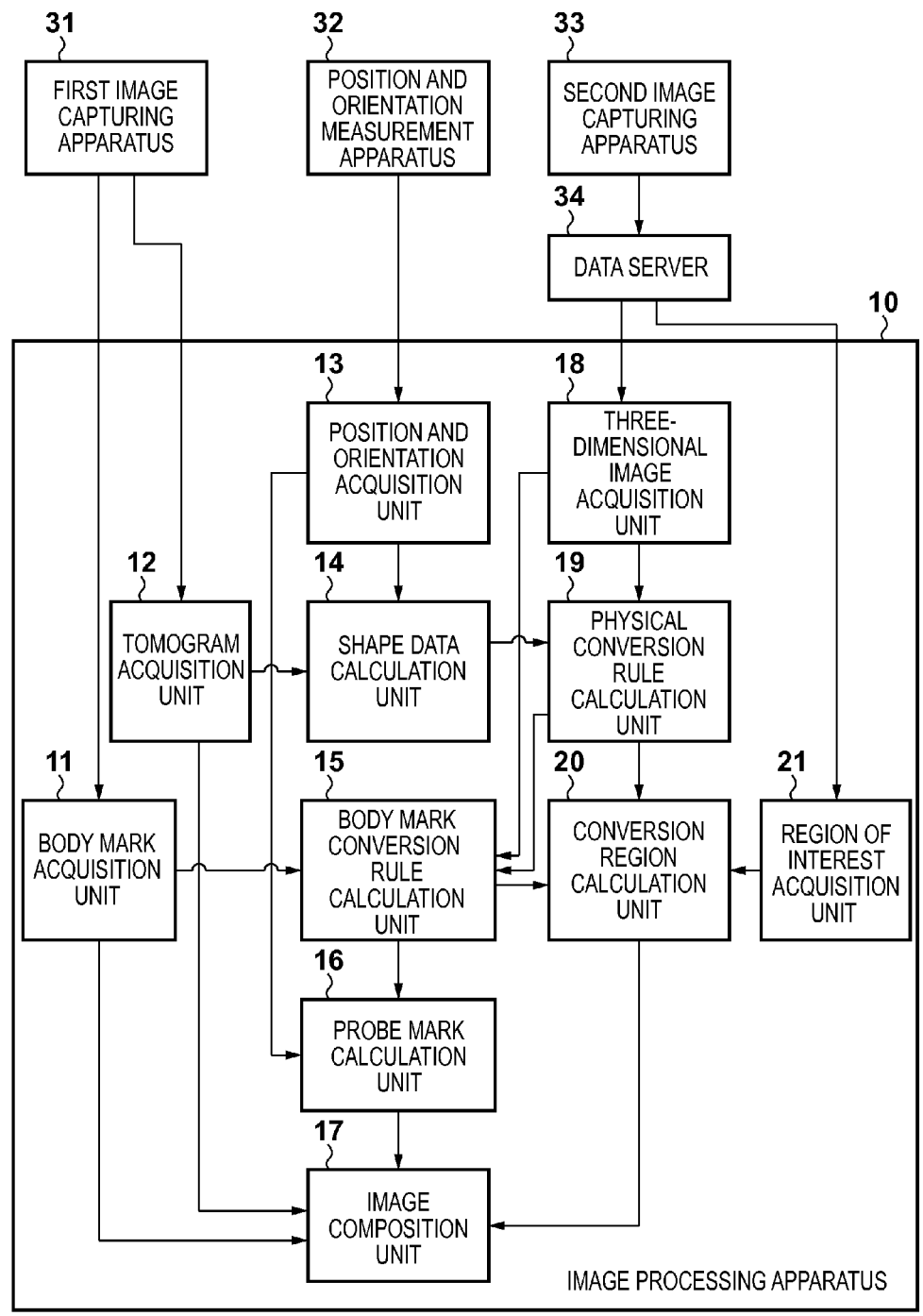
FIG. 1 is a diagram illustrating an example of the configuration of an image processing system that includes an image processing apparatus according to an embodiment of the present invention.

FIG. 1 is a diagram illustrating an example of the configuration of an image processing system that includes the image processing apparatus according to an embodiment of the present invention.

This image processing system includes a first image capturing apparatus 31, a position and orientation measurement apparatus 32, a second image capturing apparatus 33, and a data server 34. An image processing apparatus 10 is communicably connected to the first image capturing apparatus 31, the position and orientation measurement apparatus 32, and the data server 34. The image processing apparatus 10 and the second image capturing apparatus 33 communicate with each other through the data server 34.

A computer is built into each of the first image capturing apparatus 31, the position and orientation measurement apparatus 32, the second image capturing apparatus 33, and the data server 34. Each computer includes a CPU (central processing unit) or other such main control unit and a ROM (read only memory), a RAM (random access memory), an HDD (hard disk drive), or other such memory unit. The computers may also include a mouse, display, or other such input/output unit, a network card or other such communication unit, or the like. These constituent components are connected by buses or the like, and are controlled when the main control unit executes programs stored in the memory unit.

The first image capturing apparatus 31 is an ultrasound apparatus that uses ultrasonic waves to capture images, for example, and images a target object (breast) with a first shape. In this embodiment, the term "first shape" refers to the shape of the breast when the patient is facing up (supine position) with respect to the direction of gravity. Accordingly, with the first image capturing apparatus 31, the breast is imaged when the patient is in a supine position. With the first image capturing apparatus 31, the breast is imaged with the patient in a supine position by sending and receiving ultrasonic signals to and from a probe.

Figure 2:
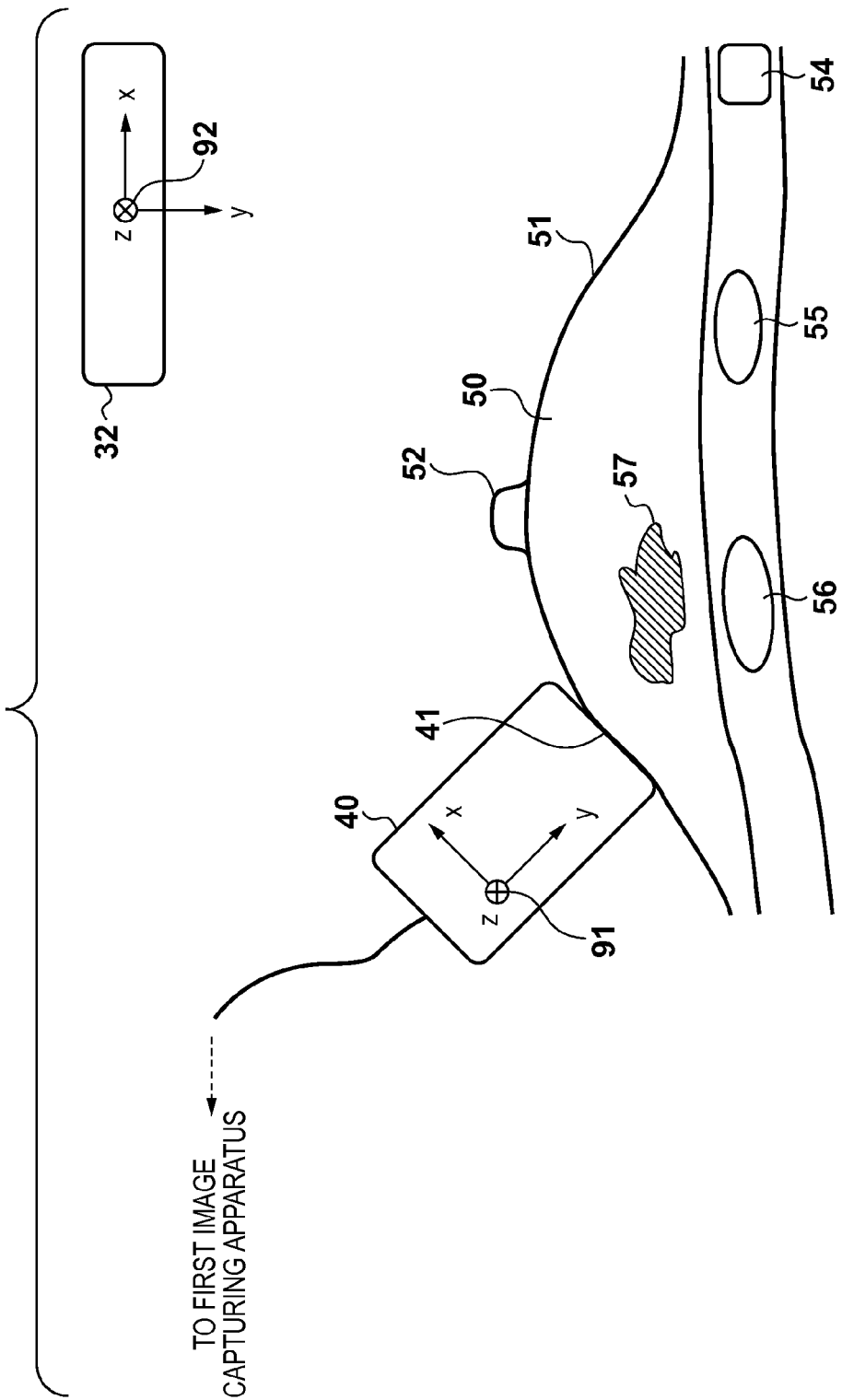
FIG. 2 is a simplified diagram of when a breast is imaged by a first image capturing apparatus 31.
Figure 3:
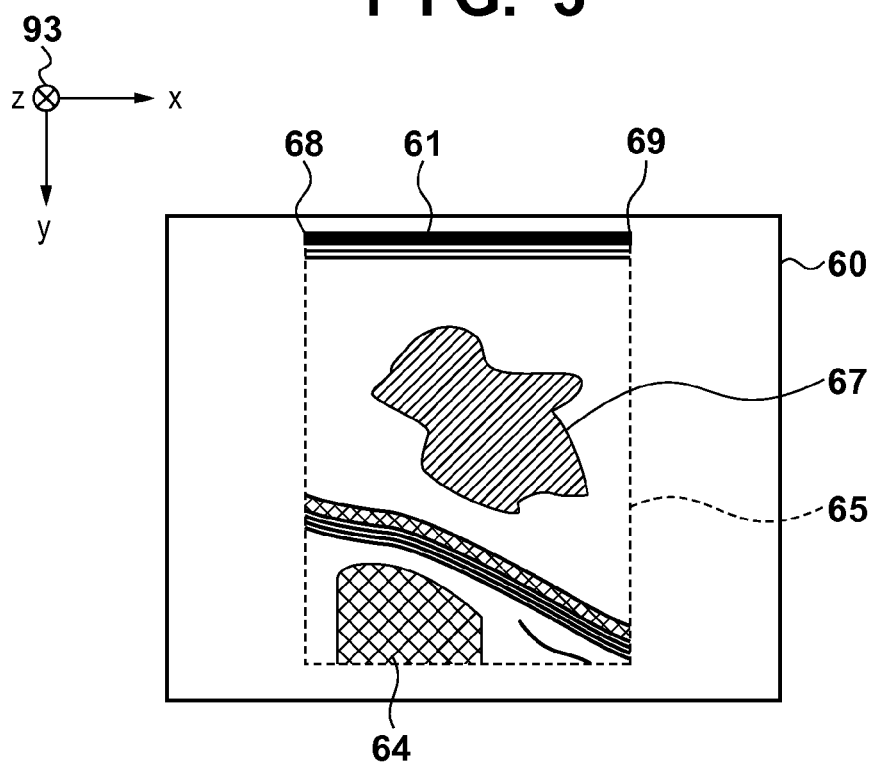
FIG. 3 is a diagram of an example of an ultrasonic tomogram.

As shown in FIG. 2, when the patient is in a supine position, imaging is performed by placing a probe 40 against the surface 51 of the breast in a supine position. Consequently, as shown in FIG. 3, an ultrasound tomogram 60 of the breast is acquired. The ultrasound tomograms 60 are sequentially inputted to the image processing apparatus 10.

Figure 4:
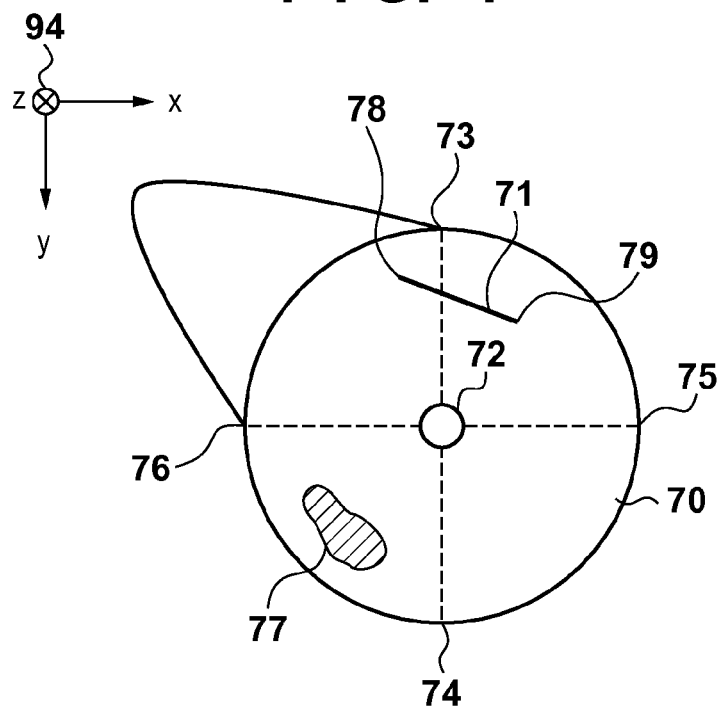
FIG. 4 is a diagram of an example of a body mark.

The first image capturing apparatus 31 holds a supine position body mark (hereinafter referred to as simply as "body mark") 70 that represents the approximate shape of the breast, shown in FIG. 4. The body mark 70 may be held in a vector image data format, for example, or it may be held in some other format, such as raster image data. FIG. 4 shows a body mark 70 that represents a breast 50, but when a diagnosis is made for another site (target object), the body mark is suitably changed according to the site to be diagnosed, etc.

Figure 5:
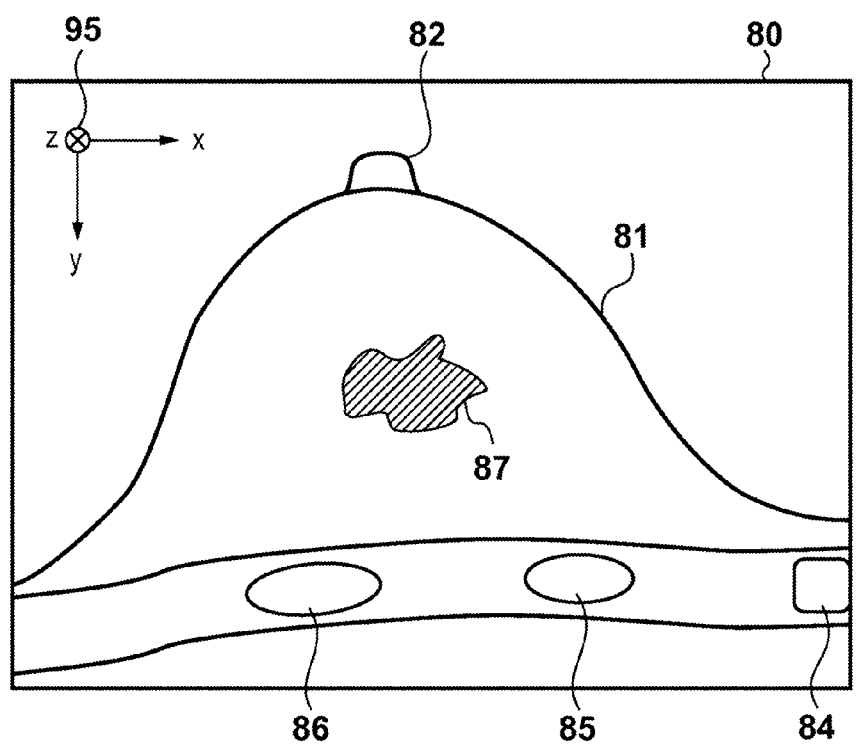
FIG. 5 is a diagram of an example of an MRI image.

The second image capturing apparatus 33 is, for example, an MRI apparatus that captures images by utilizing magnetic resonance, and images a target object with a second shape (breast). The "second shape" here means that the physical shape of the breast is different from that of the first shape, and in this embodiment, it refers to the shape of a breast in a face-down position (prone position) with respect to the direction of gravity. Accordingly, the second image capturing apparatus 33 images the breast when the patient is in a prone position. The imaging (of the breast) by the second image capturing apparatus 33 yields the MRI image 80 shown in FIG. 5 (three-dimensional medical image).

The data server 34 holds various kinds of data. For example, the MRI image 80 captured by the second image capturing apparatus 33, and shape data indicating the position and shape of a lesion region 87 within the MRI image 80 are held in the data server 34. The MRI image 80 and the shape data about the lesion region 87 are inputted to the image processing apparatus 10.

The position and orientation measurement apparatus 32 measures the position and orientation of the probe 40 connected to the first image capturing apparatus 31. The position and orientation measurement apparatus 32 is, for example, a Fastrak made by the US firm of Polhemus, and measures the position and orientation of the probe 40 using the sensor coordinate system 92 shown in FIG. 2 (a coordinate system set up as a reference by the position and orientation measurement apparatus 32) as a reference. Information (position and orientation data) indicating the position and orientation of the probe 40 is sequentially inputted to the image processing apparatus 10. The position and orientation measurement apparatus 32 may measure the position and orientation by any method, so long as the position and orientation of the probe 40 can be measured.

The image processing apparatus 10 processes various kinds of image. Here, the functional components of the image processing apparatus 10 include a body mark acquisition unit 11, a tomogram acquisition unit 12, a position and orientation acquisition unit 13, a shape data calculation unit 14, a body mark conversion rule calculation unit 15, a probe mark calculation unit 16, and an image composition unit 17. The image processing apparatus 10 also includes a three-dimensional image acquisition unit 18, a physical conversion rule calculation unit 19, a conversion region calculation unit 20, and a region of interest acquisition unit 21.

The body mark acquisition unit 11 acquires the body mark 70 held in the first image capturing apparatus 31. The acquired body mark 70 is outputted to the body mark conversion rule calculation unit 15 and the image composition unit 17.

The tomogram acquisition unit 12 acquires the ultrasound tomograms 60 (of a breast in a prone position) sequentially inputted from the first image capturing apparatus 31. The acquired ultrasound tomograms 60 are outputted to the shape data calculation unit 14 and the image composition unit 17.

The position and orientation acquisition unit 13 sequentially acquires the position and orientation data about the probe 40 inputted sequentially from the position and orientation measurement apparatus 32. The acquired position and orientation data is outputted to the shape data calculation unit 14 and the probe mark calculation unit 16.

The three-dimensional image acquisition unit 18 acquires the MRI image 80 (of a breast in the prone position) inputted from the second image capturing apparatus 33. The acquired MRI image 80 is outputted to the physical conversion rule calculation unit 19 and the body mark conversion rule calculation unit 15.

The region of interest acquisition unit 21 acquires shape data indicating the position and shape of the lesion region 87 (of a breast in the prone position) inputted from the data server 34. The region of interest can be, for example, a region designated by a physician who has read an MRI image. The acquired shape data is outputted to the conversion region calculation unit 20.

The shape data calculation unit 14 calculates shape data indicating the position and shape of the breast 50 in a supine position on the basis of the ultrasound tomogram 60 and position and orientation data about the probe 40. The calculated shape data is outputted to the physical conversion rule calculation unit 19.

The physical conversion rule calculation unit 19 calculates a physical conversion rule for converting the shape of the surface 81 of a breast in a prone position within the MRI image 80 so that this shape will substantially coincide with the shape data calculated by the shape data calculation unit 14. Specifically, it calculates a physical conversion rule for converting the shape of the surface 81 of a breast in a prone position (in a second shape) so that this shape will substantially coincide with the shape of the surface 51 of the breast in a supine position (in a first shape). The calculated physical conversion rule is outputted to the conversion region calculation unit 20.

The body mark conversion rule calculation unit 15 calculates a body mark conversion rule for converting the shape of the breast in a supine position so that this shape will substantially coincide with the shape of the body mark 70 (normalizing conversion). The calculated body mark conversion rule is outputted to the conversion region calculation unit 20 and the probe mark calculation unit 16.

The conversion region calculation unit 20 converts the shape data for the lesion region 87 in a prone position into shape data for the lesion region in a supine position (physical conversion) on the basis of the physical conversion rule calculated by the physical conversion rule calculation unit 19. This converted shape data is then further converted into shape data for a lesion region 77 on the body mark 70, on the basis of a body mark conversion rule. This converted shape data is outputted to the image composition unit 17.

The probe mark calculation unit 16 calculates a probe mark 71 that represents the position of the probe 40 on the body mark 70, on the basis of position and orientation data about the probe 40 and the body mark conversion rule. The calculated probe mark 71 is outputted to the image composition unit 17.

The image composition unit 17 combines the body mark 70, the converted shape data for the lesion region 77, and the probe mark 71. This combined image is then combined with the ultrasound tomogram 60 and displayed on a display device (not shown).

The above is a description of an example of the configuration of an image processing system. The functional components and the various devices provided to the image processing apparatus 10 do not necessarily have to be as shown in the drawings, and some or all thereof may be constituted by some kind of device within the system. For example, the position and orientation measurement apparatus 32 may be incorporated into the image processing apparatus 10.

Figure 6:
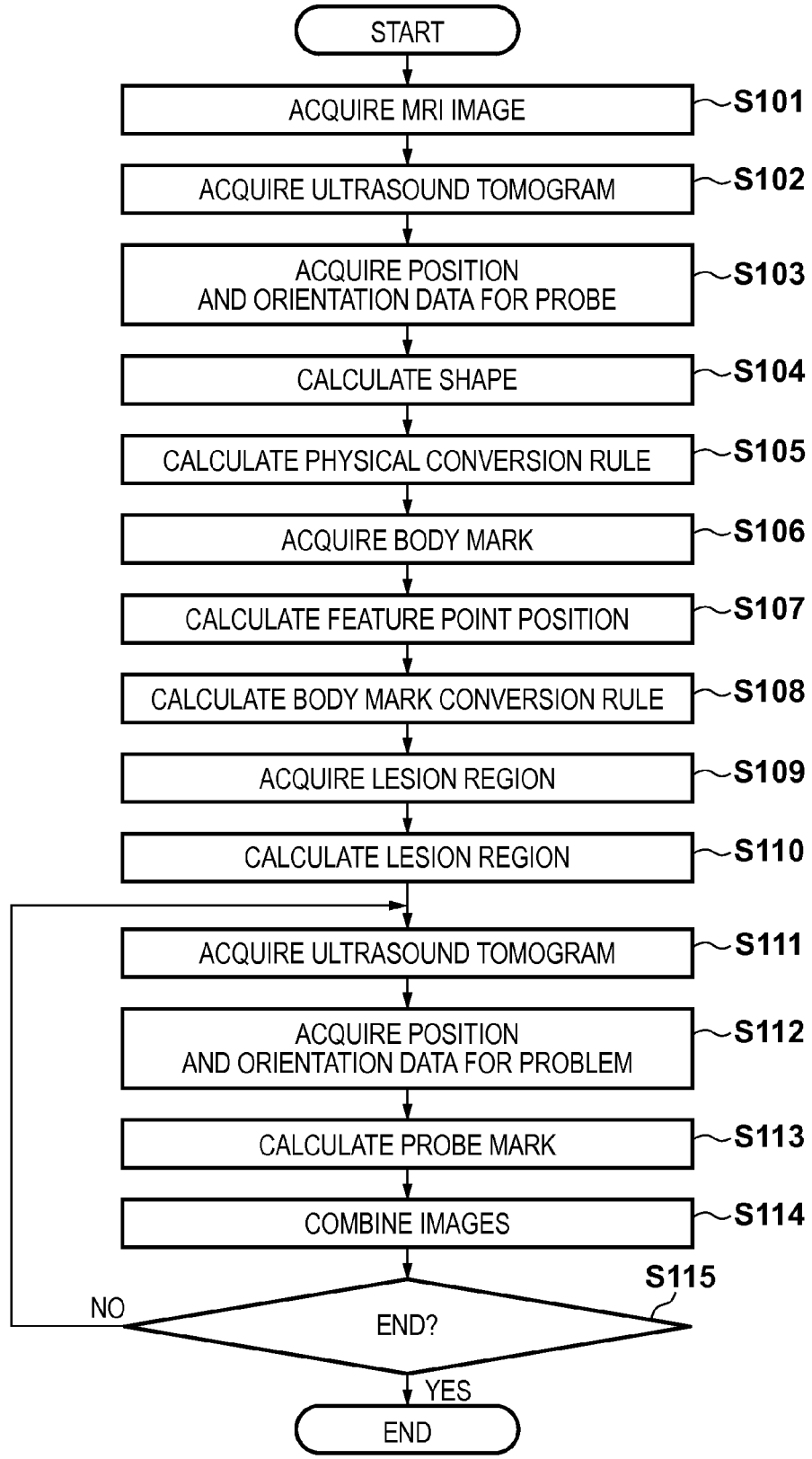
FIG. 6 is a flowchart of an example of the flow of processing of the image processing apparatus 10 shown in FIG. 1.

An example of the flow of processing of the image processing apparatus 10 shown in FIG. 1 will be described through reference to FIG. 6. This processing involves, for example, having the CPU of the image processing apparatus 10 read and execute programs stored in a ROM or the like, using a RAM as a working area.

S101

The image processing apparatus 10 first acquires the MRI image 80 of a breast in a prone position from the data server 34 in the three-dimensional image acquisition unit 18. In this embodiment, it is assumed that the surface 81 of the breast has already been extracted from within the MRI image 80 as the shape of the breast in a prone position. Also, in this embodiment, a papilla 82, a breast upper end (not shown), a breast lower end (not shown), a breast left end (not shown), and a breast right end (not shown) are used as feature points of the breast in a prone position. We shall also assume that the position $X_{I_k}^{Prone}$ ($1 \leq I_k \leq I_n$) of these feature points has already been extracted from the MRI image 80 in a prone position. The shape of the breast in a prone position, and information related to these feature points are simultaneously acquired from the data server 34 during the acquisition of the MRI image 80. $I_k$ indicates an index previously allotted to each of the feature points, and $I_n$ indicates the number of feature points ("5" in this embodiment).

S102

The image processing apparatus 10 uses the tomogram acquisition unit 12 to acquire the ultrasound tomograms 60 sequentially inputted from the first image capturing apparatus 31 to the image processing apparatus 10.

S103

The image processing apparatus 10 uses the position and orientation acquisition unit 13 to acquire position and orientation data for the probe 40 sequentially inputted from the position and orientation measurement apparatus 32 to the image processing apparatus 10.

S104

The image processing apparatus 10 uses the shape data calculation unit 14 to acquire the shape of the breast in a supine position. More specifically, the operator acquires the position coordinate vectors at the instant the center part 41 of the tip of the probe 40 is brought into contact with a plurality of locations on the surface 51 of the breast in a supine position. It is assumed that the shape of the breast in a supine position is expressed as a group of these position coordinate vectors.

S105

The image processing apparatus 10 uses the physical conversion rule calculation unit 19 to calculate a physical conversion rule for converting the shape of the breast in a prone position so that this shape substantially coincides with the shape of the breast in a supine position.

In this processing, first a rigid body conversion rule from the prone position to the supine position is calculated on the basis of a rigid body portion of the breast in a prone position (such as a rib 84 within the MRI image 80) and a rigid body portion of the breast in a supine position (such as a rib 64 within the ultrasound tomogram 60). The ICP (iterative closest point) method or another known method may be used for this calculation processing.

Then, a non-rigid body conversion rule for performing conversion of the shape of the breast in a prone position that takes physical deformation into account is calculated so that this shape substantially coincides with the shape of the breast in a supine position. This non-rigid body conversion rule is expressed as a group of three-dimensional displacement vectors that represent the amount of movement when the pixels that make up the MRI image 80 move to corresponding positions during conversion of an image from a prone position to a supine position.

A method based on gravitational deformation simulation, for example, may be used to calculate the non-rigid body conversion rule (see Literature 3). In this embodiment, the physical conversion rule from the prone position to the supine position is made up of the above-mentioned rigid body conversion rule and non-rigid body conversion rule.

S106

The image processing apparatus 10 uses the body mark acquisition unit 11 to acquire the body mark 70 that represents the approximate shape of the breast from the first image capturing apparatus 31. In this embodiment, a papilla 72, a breast upper end 73, a breast lower end 74, a breast inner end 75, and a breast outer end 76 are used as feature points of the body mark 70. It is assumed that the position $X_{Ik}^{Bodymark}$ ($1 \le I_k \le I_n$) of these feature points is extracted ahead of time, and that the body mark acquisition unit 11 acquires it along with the body mark 70 from the first image capturing apparatus 31. It is assumed that these feature points are represented by a body mark coordinate system 94 (a coordinate system in which a plane including the body mark is defined as the XY plane, and an axis perpendicular to this as the Z axis), and in this embodiment it is assumed that this position is present only in the XY plane.

S107

The image processing apparatus 10 uses the body mark conversion rule calculation unit 15 to perform calculation processing on the position of the feature points. More specifically, the position $X_{Ik}^{Prone}$ ($1 \le I_k \le I_n$) of the breast in a prone position is converted into the position $X_{Ik}^{Supine}$ ($1 \le I_k \le I_n$) of the breast in a supine position on the basis of the physical conversion rule calculated by the processing of S105.

S108

The image processing apparatus 10 uses the body mark conversion rule calculation unit 15 to calculate a body mark conversion rule for converting the shape of the breast in a supine position so that this shape will substantially coincide with the shape of the body mark 70. More specifically, a body mark conversion rule is calculated for converting so that the position $X_{Ik}^{Supine}$ of the breast in a supine position corresponds to the position $X_{Ik}^{Bodymark}$ the feature point of the body mark 70. The method disclosed in Literature 1, for example, may be used to calculate the body mark conversion rule. The body mark conversion rule is expressed by a three-dimensional displacement vector group representing the amount of movement by various points on the breast in a supine position up to the corresponding position in the XY plane in the body mark coordinate system 94, during conversion of the position of the feature points.

S109

The image processing apparatus 10 uses the region of interest acquisition unit 21 to acquire shape data for the lesion region 87 in a prone position inputted from the data server 34 to the image processing apparatus 10. In this embodiment, the lesion region 87 in a prone position is acquired as a label image of the same size as the MRI image 80 of the breast in a prone position, and is expressed as $I_{Lesion}^{Prone}$ (x, y, z). $I_{Lesion}^{Prone}$ (x, y, z) is a scalar function having a value of either 1 or 0 and representing whether or not the position coordinate vector $X^{Prone}$ (x, y, z) in an MRI image coordinate system 95 represents a lesion region.

S110

The image processing apparatus 10 uses the conversion region calculation unit 20 to calculate the lesion region 77 in the body mark coordinate system 94. Specifically, the position coordinate vectors $X_{Vk}^{Prone}$ ($1 \le V_k \le V_n$) at which $I_{Lesion}^{Prone}$ (x, y, z)=1 are each converted using a physical conversion rule and a body mark conversion rule. As a result, the position coordinate vectors $X_{Vk}^{Bodymark}$ in the body mark coordinate system 94 are calculated. $V_n$ is the number of pixels that make up the lesion region 87 in a prone position. After this, the region represented by the position coordinate vectors $X_{Vk}^{Bodymark}$ is set as the lesion region 77 in the body mark coordinate system 94.

S111

The image processing apparatus 10 uses the tomogram acquisition unit 12 to acquire the ultrasound tomograms 60 sequentially inputted from the first image capturing apparatus 31 to the image processing apparatus 10.

S112

The image processing apparatus 10 uses the position and orientation acquisition unit 13 to acquire position and orientation data for the probe 40 in the sensor coordinate system 92 sequentially inputted from the position and orientation measurement apparatus 32 to the image processing apparatus 10.

S113

The image processing apparatus 10 uses the probe mark calculation unit 16 to calculate a probe mark. More specifically, the positions of the left end part 68 and right end part 69 of the probe tip within the ultrasound tomograms 60 are converted into the positions of the left end part 78 and right end part 79 of the probe tip in the body mark coordinate system 94 on the basis of a body mark conversion rule. We will let the line segment connecting the position of the left end part 78 and the position of the right end part 79 be the probe mark 71.

S114

The image processing apparatus 10 uses the image composition unit 17 to combine and display the lesion region 77 and the probe mark 71 on the body mark 70. This body mark 70 is then superposed in a display at a specific position on the ultrasound tomogram 60 acquired in the processing of S111.

S115

The image processing apparatus 10 determines whether or not to end the processing. For example, it determines to end the processing if the operator has clicked an end button disposed on the display unit (not shown) with a mouse or the like. If it determines to end the processing, the image processing apparatus 10 ends this processing, and otherwise the processing returns to S111 and the same processing as above is performed on the newly acquired ultrasound tomogram 60 and the position and orientation data of the probe 40.

As described above, with this embodiment, a lesion region (region of interest) within an MRI image taken in a prone position is converted into the shape when the image is captured in a supine position, and this converted lesion region can be combined and displayed at a suitable position on the body mark. Also, the position and orientation of the probe during imaging in a supine position can also be displayed at a suitable position on the body mark.

This allows the operator to operate the probe while referring to the positional relation between the region of interest and the probe. Also, this aids the production of medical documents that allow the positional relation between the region of interest and the probe to be easily grasped.

Embodiment 2

Embodiment 2 will now be described. In Embodiment 2 we will describe a case in which, in addition to the processing described in Embodiment 1, no physical conversion is performed on the shape of the lesion region imaged in a prone position, and only normalizing conversion to a body mark (body mark conversion) is performed to display the lesion region on the body mark. Specifically, with the combined display according to Embodiment 2, the lesion region imaged in a prone position is combined in a display along with the lesion region described in Embodiment 1 (see FIG. 8). The image processing apparatus according to Embodiment 2 will now be described, putting emphasis on differences from Embodiment 1.

Figure 7:
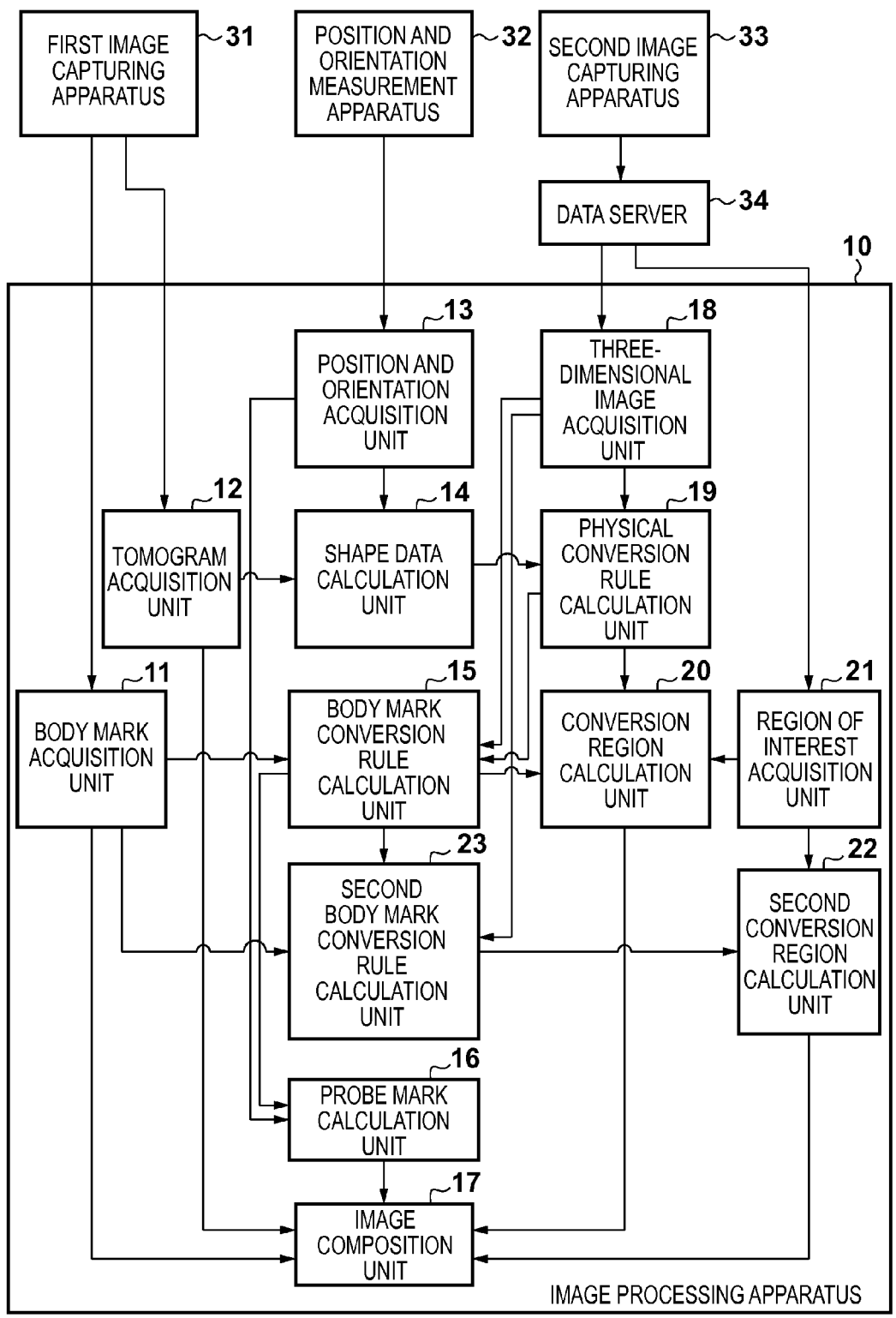
FIG. 7 is a diagram of an example of the configuration of the image processing apparatus 10 according to Embodiment 2.

FIG. 7 is a diagram of an example of the configuration of the image processing apparatus 10 according to Embodiment 2. Those components that are the same as in FIG. 1 and described in Embodiment 1 will be numbered the same, and may not be described again.

With the image processing apparatus 10 according to Embodiment 2, a second body mark conversion rule calculation unit 23 and a second conversion region calculation unit 22 are provided in addition to the components shown in FIG. 1.

The second body mark conversion rule calculation unit 23 calculates a conversion rule for converting (normalizing conversion) the shape of a breast in a prone position acquired by the three-dimensional image acquisition unit 18 so that the shape substantially coincides with the shape of the body mark 70 acquired by the body mark acquisition unit 11. This conversion rule (second body mark conversion rule) is outputted to the second conversion region calculation unit 22.

The second conversion region calculation unit 22 converts shape data for the lesion region 87 in a prone position acquired by the region of interest acquisition unit 21 into shape data for the lesion region on the body mark 70 on the basis of the second body mark conversion rule. This shape data is outputted to the image composition unit 17.

The image composition unit 17 combines the body mark 70, the probe mark 71, and the shape data for the regions calculated by the conversion region calculation unit 20 and the second conversion region calculation unit 22. Then, the combined image and the ultrasound tomogram 60 are combined and displayed.

Figure 8:
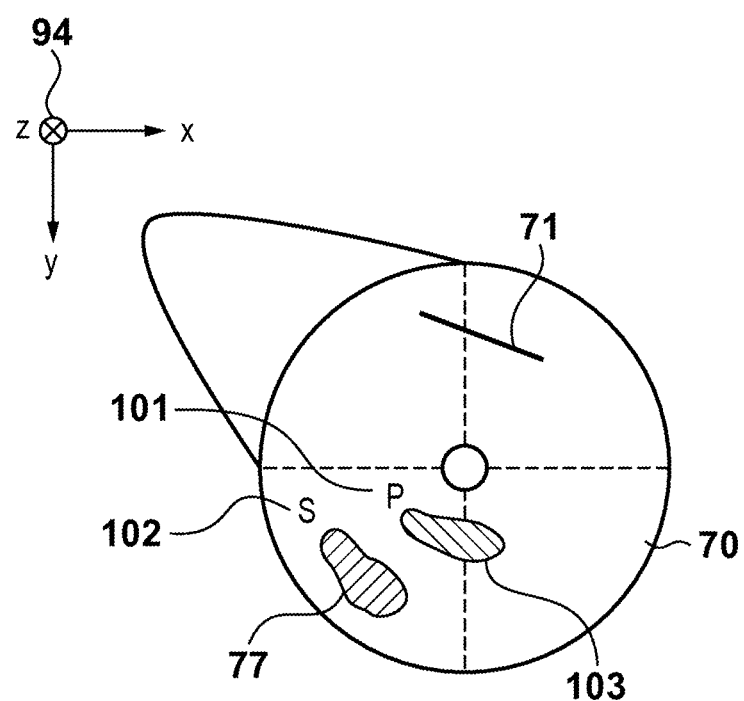
FIG. 8 is a diagram of an example of a body mark according to Embodiment 2.

FIG. 8 is a diagram of an example of a body mark displaying shape data for the regions calculated by the conversion region calculation unit 20 and the second conversion region calculation unit 22. Ports that are the same as in FIG. 4 and described in Embodiment 1 will be numbered the same.

In Embodiment 2, a lesion region 103 in a prone position is displayed in addition to the same lesion region 77 as in Embodiment 1, on the body mark 70. Also, a supine position mark 102 is displayed corresponding to the lesion region 77, and a prone position mark 101 is also displayed corresponding to the lesion region 103.

Next, an example of the flow of processing of the image processing apparatus 10 according to Embodiment 2 will be described through reference to FIG. 9. This processing involves, for example, having the CPU of the image processing apparatus 10 read and execute programs stored in a ROM or the like, using a RAM as a working area, just as in Embodiment 1. The basic flow of processing is the same as in FIG. 6 and described in Embodiment 1, so the description here will focus on what is different in the processing.

What is different in the processing here is that the processing of S201 to S203 is added.

S201

The image processing apparatus 10 uses the second body mark conversion rule calculation unit 23 to calculate a second body mark conversion rule for converting the shape of a breast in a prone position so that this shape substantially coincides with the shape of the body mark 70. More specifically, it calculates a rule for converting so that the position $X_{lk}^{Prone}$ of the feature points of a breast in a prone position calculated by the processing in S107 corresponds to the position $X_{lk}^{Bodymark}$ of the feature points of the body mark 70. The method disclosed in Literature 1, for example, may be used to calculate the second body mark conversion rule. The second body mark conversion rule is expressed by a three-dimensional displacement vector group representing the amount of movement by various points on the breast in a prone position up to the corresponding position in the XY plane in the body mark coordinate system 94, during conversion of the position of the feature points.

S202

The image processing apparatus 10 uses the second conversion region calculation unit 22 to calculate the shape of the lesion region 103 in a prone position in the body mark coordinate system 94. In this processing, first the position coordinate vectors $X_{Vk}^{Prone}$ ($1 \leq V_k \leq V_n$) at which $I_{Lesion}^{Prone}$ (x, y, z)=1 are each converted using a second body mark conversion rule. The position coordinate vectors $X'_{Vk}^{Bodymark}$ in the body mark coordinate system 94 are then calculated. Finally, the region expressed by the position coordinate vectors $X'_{Vk}^{Bodymark}$ is set as the lesion region 103 in the body mark coordinate system 94.

S203

The image processing apparatus 10 uses the image composition unit 17 to combine the lesion region 77 and the probe mark 71 in a display on the body mark 70, just as in Embodiment 1. In addition, the lesion region 103 in a prone position and the prone position mark 101 (such as the letter P, which is the first letter of prone) are also displayed. Further, the supine position mark 102 (such as the letter S, which is the first letter of supine) may be displayed along with the lesion region 77. After this, the body mark 70 is displayed superposed over the ultrasound tomogram 60 acquired in the processing of S111.

As described above, with Embodiment 2, regions of interest of a target object imaged in different physical shapes can be simultaneously displayed on a single body mark. Consequently, the operator can operate the probe while referring to the positional relation of regions of interest of different physical shapes. Also, this aids the production of medical documents that allow the positional relation between regions of interest of different physical shapes to be easily grasped.

Embodiment 3

Next, Embodiment 3 will be described. In Embodiment 3 we will describe a case in which a supine position body mark and a prone position body mark are both displayed. Only those parts of the image processing apparatus according to Embodiment 3 that differ from those in Embodiments 1 and 2 will be described.

FIG. 10 is a diagram of an example of a body mark used for a prone position. In Embodiment 3, a prone position body mark 110 is described as having the same shape as the supine position body mark 70.

Figure 11:
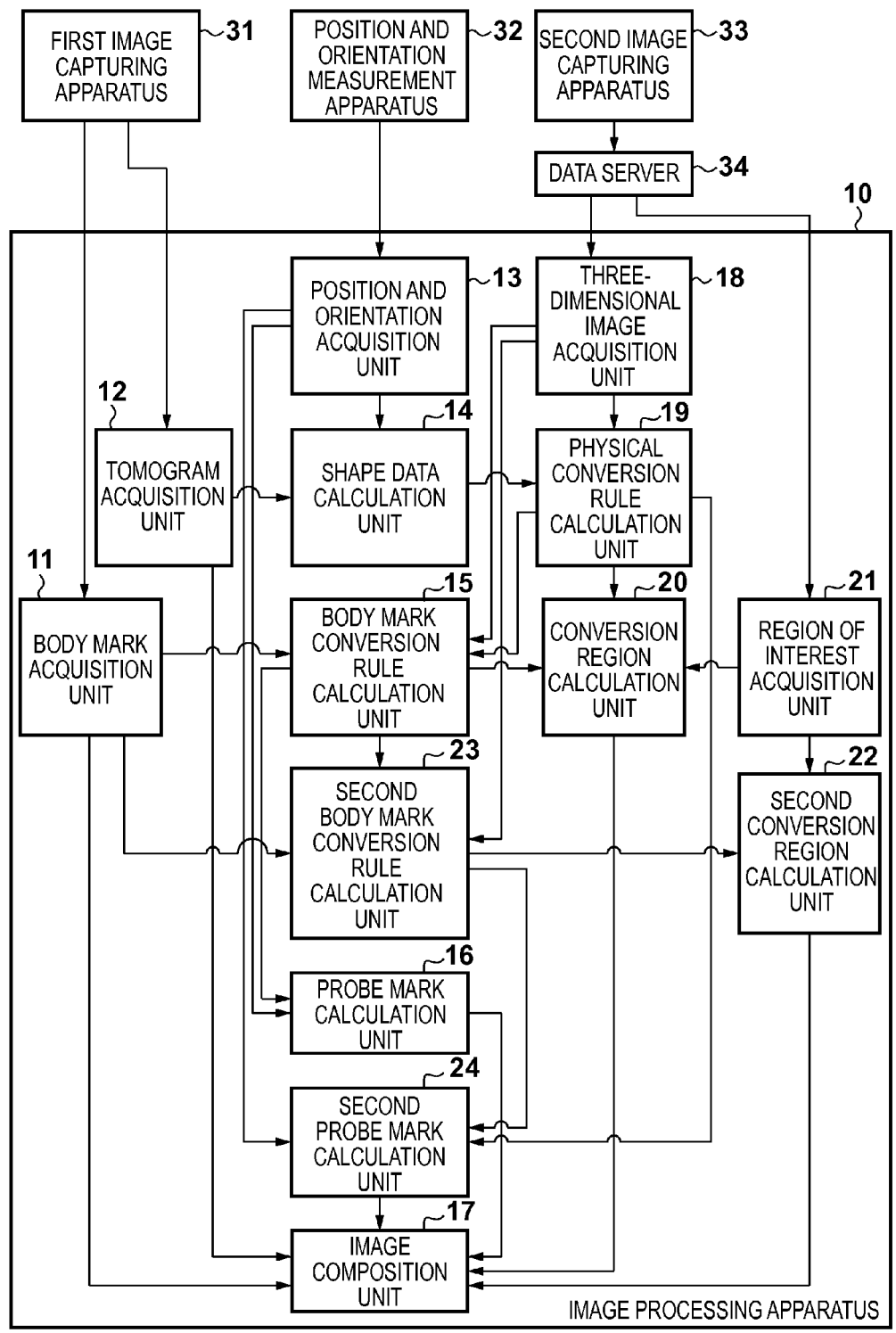
FIG. 11 is a diagram of an example of the configuration of the image processing apparatus 10 according to an Embodiment 3.

FIG. 11 is a diagram of an example of the configuration of the image processing apparatus 10 according to an Embodiment 3. Those components that are the same as in FIG. 7 and described in Embodiment 2 will be numbered the same, and may not be described again.

With the image processing apparatus 10 according to Embodiment 3, a second probe mark calculation unit 24 is provided in addition to the components shown in FIG. 7.

Just as in Embodiment 2, the body mark acquisition unit 11 here acquires the supine position body mark 70 inputted to the image processing apparatus 10, and outputs it to the body mark conversion rule calculation unit 15 and the image composition unit 17. Furthermore, the body mark acquisition unit 11 acquires the prone position body mark 110 and outputs it to the second body mark conversion rule calculation unit 23 and the image composition unit 17.

The second body mark conversion rule calculation unit 23 calculates a second body mark conversion rule for converting (normalizing conversion) the shape of a breast in a prone position acquired by the three-dimensional image acquisition unit 18 so that the shape substantially coincides with the shape of the prone position body mark 110. This second body mark conversion rule is outputted to the second conversion region calculation unit 22 and the second probe mark calculation unit 24.

The second probe mark calculation unit 24 inputs the position and orientation data for the probe 40 acquired by the position and orientation acquisition unit 13, the physical conversion rule acquired by the physical conversion rule calculation unit 19, and the second body mark conversion rule. A probe mark 111 on the prone position body mark 110 is then calculated on the basis of this information and outputted to the image composition unit 17.

The image composition unit 17 combines the supine position body mark 70, the shape data for the region calculated by the conversion region calculation unit 20, and the supine position probe mark 71. Also, the image composition unit 17 combines the prone position body mark 110, the shape data for the region calculated by the second conversion region calculation unit 22, and the prone position probe mark 111. These are combined with the ultrasound tomogram 60 and displayed. After this, information representing the physical shapes of these body marks (information that allows the user to identify whether each body mark represents a supine position or a prone position) is also displayed.

Figure 12:
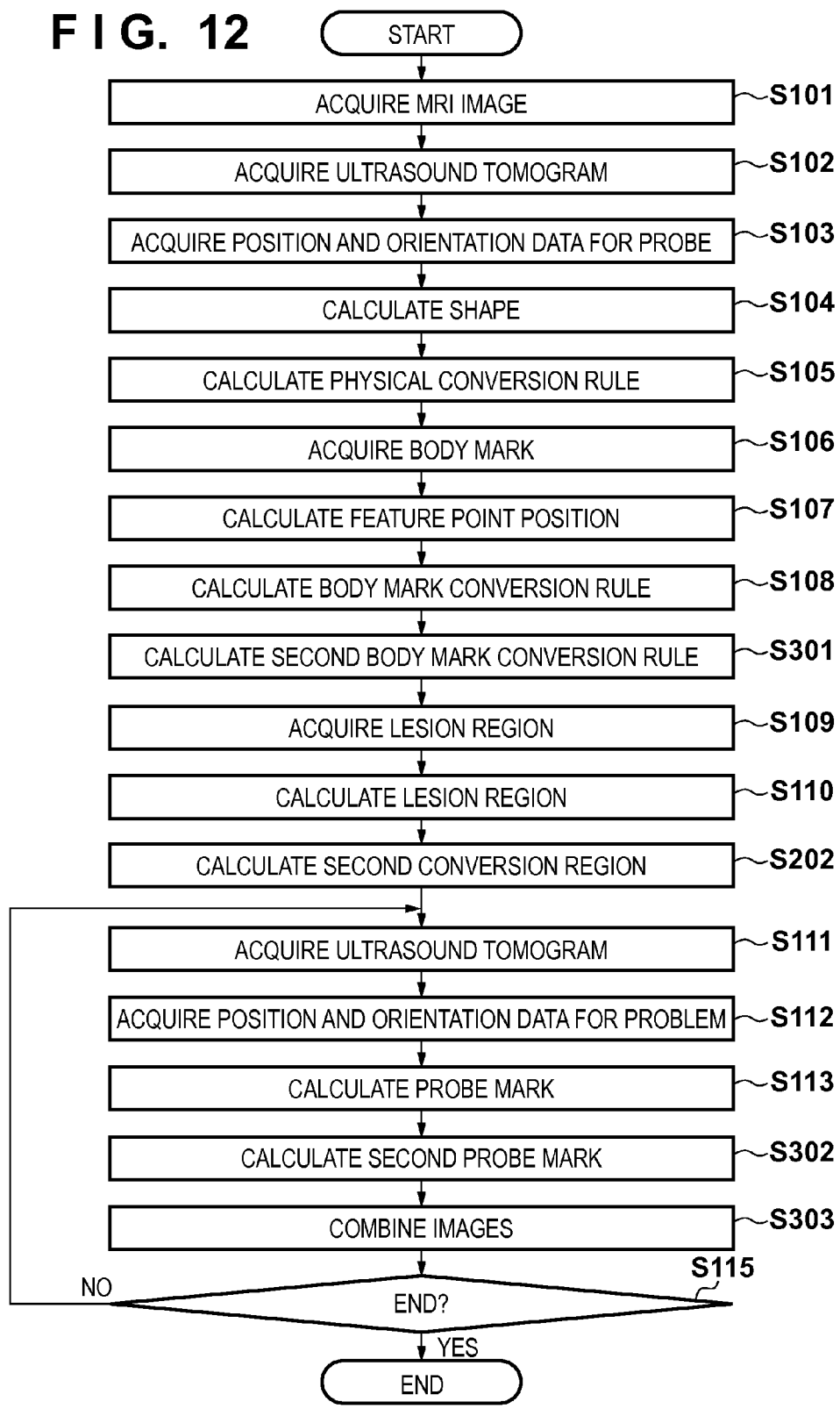
FIG. 12 is a flowchart of an example of the flow of processing of the image processing apparatus 10 according to Embodiment 3.

An example of the flow of processing of the image processing apparatus 10 according to Embodiment 3 will be described through reference to FIG. 12. This processing involves, for example, having the CPU of the image processing apparatus 10 read and execute programs stored in a ROM or the like, using a RAM as a working area, just as in Embodiment 1. The basic flow of processing is the same as in FIG. 6 and described in Embodiment 1, and the same as in FIG. 9 and described in Embodiment 2, so the description here will focus on what is different in the processing.

What is different in the processing here is that the processing of S301 to S303 is added.

S301

Figure 9:
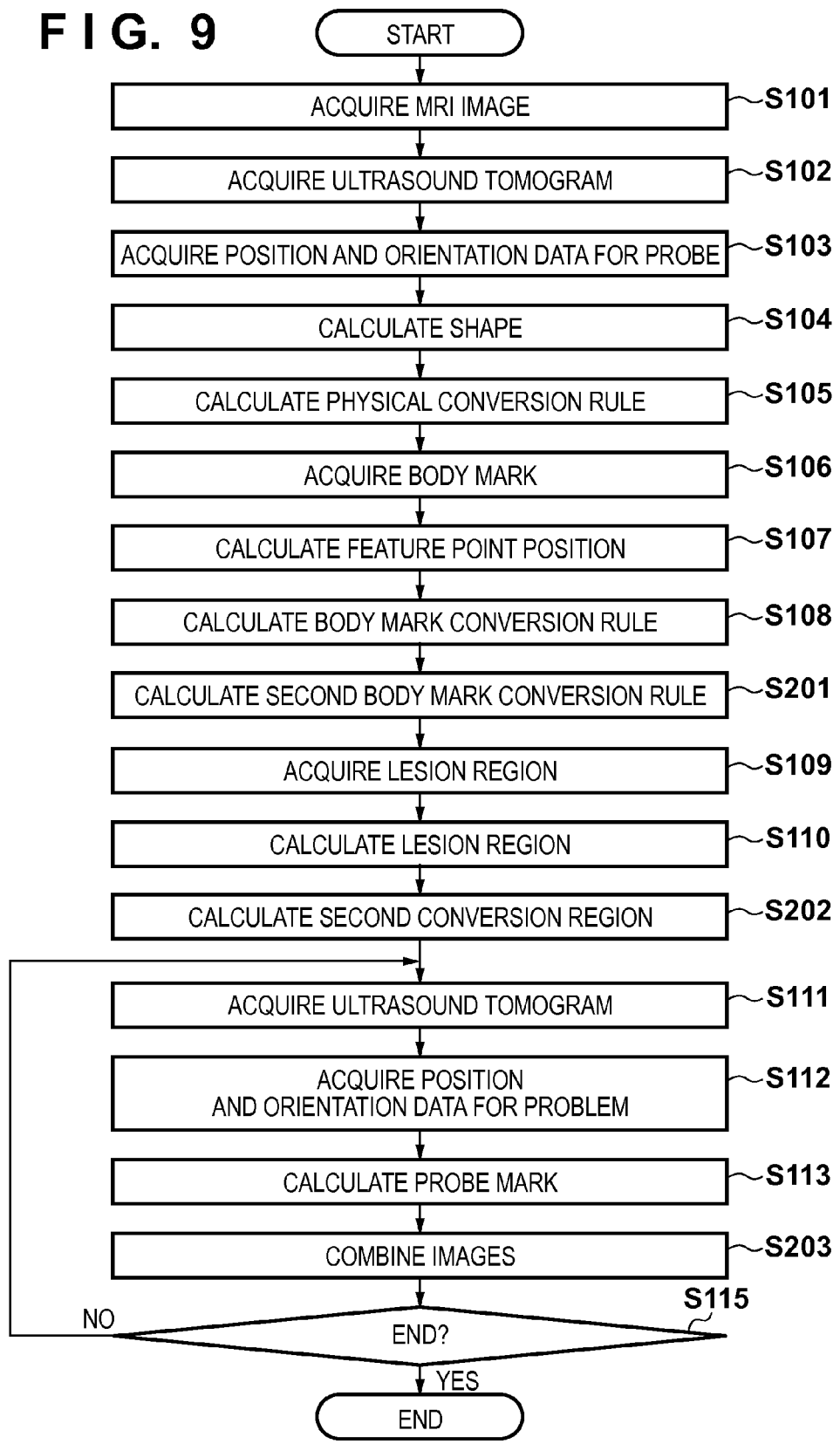
FIG. 9 is a flowchart of an example of the flow of processing of the image processing apparatus 10 according to Embodiment 2.

The image processing apparatus 10 uses the second body mark conversion rule calculation unit 23 to subject the prone position body mark 110 to the same processing as in S201 described through reference to FIG. 9 in Embodiment 2 above. Consequently, a second body mark conversion rule is calculated for converting the shape of the breast in a prone position so that this shape will substantially coincide with the shape of the prone position body mark 110.

S302

The image processing apparatus 10 uses the second probe mark calculation unit 24 to calculate a second probe mark. More specifically, the positions of the left end part 68 and right end part 69 of the probe tip within the ultrasound tomogram 60 are converted into the positions of the left end part 118 and right end part 119 of the probe tip in a body mark coordinate system 96 on the basis of a physical conversion rule and a second body mark conversion rule. In Embodiment 3, the physical conversion rule from prone position to supine position is converted into a physical conversion rule from supine position to prone position. It is assumed that the probe mark 111 is a line segment connecting the positions of the left end part 118 and the right end part 119.

S303

As shown in FIG. 13, the image processing apparatus 10 uses the image composition unit 17 to display both the supine position body mark 70 and the prone position body mark 110 next to each other. More specifically, the lesion region 77 and the probe mark 71 are displayed on the supine position body mark 70. Information indicating the supine position body mark 70 (such as a supine position mark 121 consisting of the letter S, which is the first letter of supine) is also displayed.

Further, a lesion region 117 and the probe mark 111 are displayed on the prone position body mark 110 (on the second body mark). Just as with the supine position body mark 70, information indicating the prone position body mark 110 (such as a prone position mark 116 consisting of the letter P, which is the first letter of prone) is also displayed. Finally, the supine position and prone position body marks are superposed on the ultrasound tomogram 60 acquired in the processing of S111, and these body marks are displayed next to each other. Since a breast body mark generally represents a breast in a supine position, information indicating a supine position body mark (the supine position mark 121) does not necessarily have to be displayed.

With Embodiment 3 described above, regions of interest of a target object imaged in different physical shapes can be simultaneously displayed at suitable positions on corresponding body marks.

Consequently, the operator can operate the probe while referring to the positional relation of regions of interest of different physical shapes. Also, this aids the production of medical documents that allow the positional relation between regions of interest of different physical shapes to be easily grasped.

Representative embodiments of the present invention were given above as examples, but the present invention is not limited to or by the above embodiments or what is shown in the drawings, and these can be suitably modified without departing from the gist of the invention. A few modification examples will now be given.

Modification Example 1 of Embodiment 3

In Embodiment 3 above, a case was described in which body marks for both the supine position and the prone position were displayed (next to each other), but this is not the only option. For example, just the prone position body mark 110 may be displayed, or the display of the supine position and prone position body marks may be switched at the command of the operator.

Modification Example 2 of Embodiment 3

In Embodiment 3 above, a case was described in which the supine position mark 121 or the prone position mark 116 was represented by the letter S or P as shown in FIG. 13, but this is not the only option. The supine position mark 121 or the prone position mark 116 may be any mark as long as it is information that identifies whether a supine position or a prone position is being represented. For example, as shown in FIG. 14, the mark may be a symbol in which a dot or an X is drawn within a circle (the region representing the papilla).

Modification Example 1 of Embodiments 1 to 3

In Embodiments 1 to 3 above, a case in which a human breast was the target object was described as an example, but this is not the only option, and the target object may be any site of the body.

Also, in the above embodiments, a case in which a lesion region was the region of interest was described as an example, but the region of interest is not limited to this, and may be any region at all. For instance, it may be a region that represents a treatment scar, such as a biopsy within an MRI image, or a region that represents a hematoma. There may also be a plurality of regions of interest, or the region of interest may be (the position of) a feature point having no volume.

Modification Example 2 of Embodiments 1 to 3

In Embodiments 1 to 3 above, a case in which the probe 40 was used to measure the shape of the surface 51 of a breast in a supine position (see S104) was described, but this is not the only option. For example, a range sensor or other such shape measurement apparatus may be used to measure the shape of the surface 51 of a breast in a supine position.

Modification Example 3 of Embodiments 1 to 3

In Embodiments 1 to 3 above, a case of using a two-dimensional body mark representing the approximate shape of a breast (see FIG. 4) was described, but this is not the only option. For example, a three-dimensional body mark representing the approximate shape of a breast may be used. When a three-dimensional body mark is used, there will be feature points on the body mark other than in the XY plane.

Modification Example 4 of Embodiments 1 to 3

In Embodiments 1 to 3 above, a case in which the first shape referred to the shape of a breast when the patient was face up (in a supine position) with respect to the direction of gravity, and the second shape referred to the shape of a breast when the patient was face down (in a prone position) with respect to the direction of gravity, but this is not the only option. For example, the first and second shapes may be the shape of a target object in any state, including when the patient is lying on his or her side, standing, or sitting.

Also, the first and second shapes are not limited to differences in shape attributable to the direction of gravity, and may be shapes attributable to some other factor. For example, the first and second shapes may be the result of deformation caused by pressure from a mammo coil (not shown) used in MRI, deformation caused by pressing the probe 40 against the breast during ultrasound imaging, or deformation caused by something else. Furthermore, for deformation caused by pressing the probe 40 against the breast, a distance measurement apparatus may be used which allows the shape of a breast undergoing successive deformation to be measured. In this case, if there is no determination to end the processing in S115 shown in FIGS. 6, 9, and 12, then the processing may be returned to S104 shown in FIGS. 6, 9, and 12.

Modification Example 5 of Embodiments 1 to 3

In Embodiments 1 to 3 above, a case of using an MRI apparatus as the second image capturing apparatus 33 was described, but this is not the only option. For example, an opto-acoustic tomography apparatus, an OCT (Optical Coherence Tomograph) apparatus, PET/SPECT, a three-dimensional ultrasound apparatus, or the like may be used as a second image capturing apparatus. Specifically, any apparatus may be used as long as it is able to acquire images three-dimensionally and to image a target object with a different shape from that of the target object (breast) imaged by the first image capturing apparatus 31.

Modification Example 6 of Embodiments 1 to 3

In Embodiments 1 to 3 above, a case in which probe marks were combined in a display on a body mark was described, but the probe marks do not necessarily have to be displayed.

Modification Example 7 of Embodiments 1 to 3

In Embodiments 1 to 3 above, a case in which a lesion region (region of interest) having a specific shape was combined in a display at a corresponding position on a body mark was described, but this is not the only option. For example, just the position of the region of interest may be combined in a display on the body mark.

Modification Example 8 of Embodiments 1 to 3

Embodiments of the present invention can be, for example, in the form of a system, an apparatus, a method, a program, a storage medium, or the like. More specifically, the present invention may be applied to a system made up of a position and orientation devices, or may be applied to an apparatus consisting of a single device.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-089538 filed on Apr. 13, 2011, which is hereby incorporated by reference herein in its entirety.

What is claimed is:

1. An image processing apparatus that displays a region of interest on a body mark that represents a target object, comprising:
an image acquirer configured to acquire an image of the target object in a second body posture that is different from a first body posture;
a converter which is configured to convert a position and shape of the region of interest in the target object in the second body posture into a converted position and shape of the region of interest in the target object in the first body posture, on the basis of the shape of the target object in the first body posture and the second body posture, and is configured to convert the converted position and shape of the region of interest in the target object in the first body posture into a first corresponding position and shape of the region of interest on the body mark, and is configured to convert the position and shape of the region of interest in the target object in the second body posture into a second corresponding position and shape of the region of interest on the body mark; and
an image composer configured to display, on the body mark in the body mark coordinate system
the first corresponding position and shape of the region of interest and the second corresponding position and shape of the region of interest with information for identifying body postures.

2. The image processing apparatus according to claim 1, wherein said converter comprises:
a physical converter configured to convert the position and shape of the region of interest in the target object in the second body posture into the converted position and shape in the target object in the first body posture, on the basis of the shape of the target object in the first body posture and the second body posture; and
a body mark converter configured to convert the converted position and shape of the region of interest converted by said physical converter into the first corresponding position and shape on the body mark, on the basis of the position and shape of the region of interest in the body posture and the shape of the body mark,
wherein said image composer displays, on the body mark, the region of interest in the target object in the first body posture and the region of interest in the target object in the second body posture, and
wherein the region of interest has the converted shape at the position on the body mark converted by said body mark converter.

3. The image processing apparatus according to claim 2, wherein said converter comprises:
a second body mark converter configured to convert the position and shape of the region of interest in the target object in the second body posture into the second corresponding position and shape on the body mark,
wherein said image composer further displays the region of interest having the second corresponding shape at the position on the body mark converted by said second body mark converter.

4. The image processing apparatus according to claim 2, wherein said converter comprises:
a second body mark converter configured to convert the position and shape of the region of interest in the target object in the second body posture into a corresponding position and shape on a second body mark that represents a target object of the second body posture,
wherein said image composer performs display of the region of interest having the first corresponding shape at the position on the body mark converted by said body mark converter, and/or display of the region of interest having the corresponding shape at the position on the second body mark converted by said second body mark converter.

5. The image processing apparatus according to claim 1, wherein an image of the target object in the first body posture is captured by sending and receiving ultrasonic signals to and from a probe, and
further comprising a probe mark calculator configured to calculate a probe mark that represents the position of the probe when an image of the target object in the first body posture has been captured, and
wherein said image composer further displays the probe mark on the body mark.

6. The image processing apparatus according to claim 4, wherein an image of the target object in the first body posture is captured by sending and receiving ultrasonic signals to and from a probe, and further comprising:
- a probe mark calculator configured to calculate a probe mark that represents the position of the probe when an image of the target object in the first body posture has been captured; and
- a second probe mark calculator configured to calculate a second probe mark obtained by converting the position of the probe mark into a corresponding position in the target object in the second body posture, on the basis of the shape of the target object in the first body posture and the second body posture, and
- wherein said image composer further displays the second probe mark on the second body mark.

7. The image processing apparatus according to claim 3, wherein said image composer further displays information that identifies the first region of interest in the target object in the first body posture and the second region of interest in the target object in the second body posture.

8. A processing method for an image processing apparatus that displays a region of interest on a body mark that represents a target object, the method comprising:
- acquiring an image of the target object with a second body posture that is different from a first body posture;
- converting a position and shape of the region of interest in the target object in the second body posture into a converted position and shape of the region of interest in the target object in the first body posture, on the basis of the shape of the target object in the first body posture and the second body posture, and converting the converted position and shape of the region of interest in the target object in the first body posture into a first corresponding position and shape of the region of interest on the body mark, and is configured to convert the position and shape of the region of interest in the target object in the second body posture into a second corresponding position and shape of the region of interest on the body mark; and
- displaying, on the body mark in the body mark coordinate system
- the first corresponding position and shape of the region of interest and the second corresponding position and shape of the region of interest with information for identifying body postures.

9. A non-transitory computer-readable storage medium that stores a program for causing a computer to function as an image processing apparatus that displays a region of interest on a body mark that represents a target object, the image processing apparatus comprising:
- an image acquirer configured to acquire an image of the target object in a second body posture that is different from a first body posture;
- a converter which is configured to convert a position and shape of the region of interest in the target object in the second body posture into a converted position and shape of the region of interest in the target object in the first body posture, on the basis of the shape of the target object in the first body posture and the second body posture, and is configured to convert the converted position and shape of the region of interest in the target object in the first body posture into a first corresponding position and shape of the region of interest on the body mark, and is configured to convert the position and shape of the region of interest in the target object in the second body posture into a second corresponding position and shape of the region of interest on the body mark; and
- an image composer configured to display, on the body mark in the body mark coordinate system
- the first corresponding position and shape of the region of interest and the second corresponding position and shape of the region of interest with information for identifying body postures.

* * * * *